United States Patent [19]
Wang et al.

[11] Patent Number: 6,045,909
[45] Date of Patent: Apr. 4, 2000

[54] ORTHOPAEDIC WIRES AND CABLES AND METHODS OF MAKING SAME

[75] Inventors: Kathy K. Wang, Suffern, N.Y.; Larry J. Gustavson, Dover, N.J.

[73] Assignee: Stryker Technologies Corporation, Kalamazoo, Mich.

[21] Appl. No.: 08/966,221

[22] Filed: Nov. 7, 1997

[51] Int. Cl.$^7$ .................................................... D02G 3/00
[52] U.S. Cl. ........................... 428/377; 428/379; 75/242; 128/899; 606/103
[58] Field of Search ........................... 75/232, 235, 242; 128/898, 899; 428/375, 377, 379, 371; 606/103, 232

[56] References Cited

U.S. PATENT DOCUMENTS

| | | |
|---|---|---|
| 494,664 | 4/1893 | Zullner . |
| 4,668,290 | 5/1987 | Wang et al. ................................ 75/235 |
| 4,946,644 | 8/1990 | Schumacher et al. . |
| 5,127,413 | 7/1992 | Ebert ........................................ 128/898 |

FOREIGN PATENT DOCUMENTS

| | | |
|---|---|---|
| 0 359 446 | 3/1990 | European Pat. Off. . |
| 0 649 636 A2 | 4/1995 | European Pat. Off. . |
| 2 268 518 | 1/1994 | United Kingdom . |

*Primary Examiner*—Merrick Dixon
*Attorney, Agent, or Firm*—Lerner, David, Littenberg, Krumholz & Mentlik, LLP

[57] ABSTRACT

Orthopaedic wires, cables, and methods of making them are based on the discovery that, in clinical orthopaedic applications, material toughness and fatigue strength are as important or more important than ultimate tensile strength. The wires and cables of the invention have a tensile strength lower than 280 ksi, but higher than 175 ksi. The presently preferred wires and cables have a tensile strength of 210–240 ksi. The fatigue strength of the wires and cables of the invention is between six and ten times that of other high strength cables used in orthopaedic applications. One method of making the wires and cables includes annealing high tensile strength wire or cable to reduce its tensile strength and thereby increase its fatigue strength. Another method is to cold work fully annealed wire or cable to the extent of decreasing its cross section by approximately 18%. Presently preferred wires and cables according to the invention are made from chromium-cobalt alloy, preferably wrought VITALLIUM (registered trademark) alloy.

24 Claims, 18 Drawing Sheets

Rc 56     400 X

Rc 57 400 X

Rc 55　　　　　　　　400 X

Rc 50 400 X

Rc 48     400 X

Rc 46     400 X

Rc 43　　　　　　　　　　　　400 X

Rc 41

400 X

Rc 41  400 X

Rc 41

400 X (a)　　　　　　　　(b)

(a)                  (b)

Rc 58 400 X

Rc 38 400 X

Rc 56                               400 X

Rc 60                               400 X

Rc 30  400 X

TENSILE TESTS

| | SIZE | UTS (MPa) | UTF (N) | 0.2% YS (MPa) | 0.2% YF (N) | Ef (%) | STIFFNESS | ENERGY |
|---|---|---|---|---|---|---|---|---|
| 1 HOW OLD | 2.0 | 1901.2 ± 31.1 | 3097.0 ± 29.0 | 1132.7 ± 58.4 | 1845.2 ± 111.5 | 7.5 ± 0.7 | 148.9 ± 11.2 | 115.8 ± 12.7 |
| 2 HOW 280 | 2.0 | 1959.9 ± 7.3 | 3989.9 ± 14.9 | 1005.3 ± 90.0 | 2046.4 ± 183.3 | 6.2 ± 0.3 | 178.1 ± 8.1 | 89.3 ± 5.4 |
| 3 HOW 175 | 2.0 | 1275.9 ± 0.3 | 2597.4 ± 0.7 | 634.0 ± 2.7 | 1290.7 ± 5.5 | 68.6 ± 1.4 | 209.1 ± 3.3 | 792.1 ± 16.9 |
| 4 ACUMED | 2.0 | 2073.6 ± 22.2 | 3519.3 ± 37.6 | 1559.6 ± 24.3 | 2647.0 ± 41.3 | 4.2 ± 0.1 | 197.9 ± 21.2 | 64.7 ± 3.0 |
| 5 BIODYNAMICS | 2.0 | 2068.6 ± 23.0 | 3510.8 ± 39.0 | 1505.0 ± 21.4 | 2554.2 ± 35.3 | 3.6 ± 0.4 | 206.5 ± 3.2 | 52.8 ± 8.4 |
| 6 HOW(USA) SS | 2.0 | 951.3 ± 1.4 | 2288.0 ± 3.4 | 605.9 ± 9.3 | 1457.2 ± 22.2 | 5.6 ± 0.3 | 108.0 ± 8.2 | 39.5 ± 2.5 |
| 7 HOW(UK) SS | 2.0 | 1439.7 ± 15.5 | 2389.8 ± 25.8 | 1081.6 ± 23.5 | 1795.5 ± 39.0 | 4.0 ± 0.3 | 143.1 ± 3.7 | 44.3 ± 4.3 |
| 8 HOW OLD | 1.6 | 1978.9 ± 45.7 | 1828.4 ± 42.2 | 1383.6 ± 31.4 | 1278.4 ± 29.0 | 6.0 ± 0.4 | 103.1 ± 6.0 | 95.3 ± 7.6 |
| 9 HOW 280 | 1.6 | 1910.7 ± 1.8 | 2125.1 ± 2.0 | 1290.5 ± 15.1 | 1435.3 ± 16.8 | 7.0 ± 0.7 | 99.3 ± 9.9 | 103.2 ± 3.1 |
| 10 ACUMED | 1.6 | 2134.8 ± 10.1 | 2374.3 ± 11.2 | 1756.2 ± 38.0 | 1953.3 ± 42.3 | 3.2 ± 0.3 | 140.7 ± 5.9 | 49.9 ± 5.4 |
| 11 BIODYNAMICS | 1.6 | 1899.1 ± 13.3 | 2367.9 ± 16.6 | 1531.9 ± 23.4 | 1910.0 ± 29.2 | 3.3 ± 0.4 | 152.6 ± 15.5 | 44.7 ± 5.9 |
| 12 ZIMMER CrCo | 1.6 | 1104.8 ± 13.3 | 1377.5 ± 16.6 | 487.3 ± 1.9 | 607.5 ± 2.4 | 65.3 ± 6.5 | 138.8 ± 10.3 | 607.8 ± 72.5 |
| 13 ZIMMER Ti | 1.6 | 451.7 ± 0.5 | 445.0 ± 0.5 | 308.3 ± 0.8 | 303.7 ± 0.8 | 14.7 ± 0.2 | 64.4 ± 5.8 | 61.6 ± 1.0 |
| 14 HOW(USA) SS | 1.6 | 1057.1 ± 1.1 | 1468.5 ± 1.5 | 835.2 ± 3.9 | 1160.3 ± 5.4 | 3.1 ± 0.1 | 93.8 ± 2.6 | 23.0 ± 1.4 |
| 15 HOW(UK) SS | 1.6 | 1576.0 ± 11.9 | 1409.0 ± 10.7 | 1313.5 ± 17.8 | 1174.4 ± 15.9 | 2.8 ± 0.1 | 88.9 ± 1.7 | 31.1 ± 0.7 |
| 16 RICHARDS Ti | 1.2 | 1004.0 ± 15.5 | 648.6 ± 10.4 | 895.7 ± 1.2 | 578.5 ± 0.8 | 5.4 ± 1.9 | 42.7 ± 1.6 | 46.2 ± 19.9 |

FIG. 22

FATIGUE TESTS

| | SIZE | TEST #1 | TEST #2 | TEST #3 | TEST #4 | AVERAGE | STD | MINIMUM | MIN/AVG(%) |
|---|---|---|---|---|---|---|---|---|---|
| 1 HOW OLD | 2.0 | 89576.0 | 69903.0 | 69626.0 | 78876.0 | 76995.3 | 8161.2 | 69626.0 | 90.4 |
| 2 HOW 280 | 2.0 | 131998.0 | 142005.0 | 122533.0 | 157296.0 | 138458.0 | 12872.3 | 122533.0 | 88.5 |
| 3 HOW 175 | 2.0 | 1329659.0* | 1000634.0* | 1012500.0* | 625468.0 | 992065.3 | 249426.4 | 625468.0 | 63.0 |
| 4 ACUMED | 2.0 | 33544.0 | 32254.0 | 44864.0 | 38857.0 | 37379.8 | 4979.5 | 32254.0 | 86.3 |
| 5 BIODYNAMICS | 2.0 | 30600.0 | 47199.0 | 40539.0 | 37598.0 | 38984.0 | 5960.6 | 30600.0 | 78.5 |
| 6 HOW(USA) SS | 2.0 | 59792.0 | 96076.0 | 75408.0 | 108992.0 | 85067.0 | 18879.4 | 59792.0 | 70.3 |
| 7 HOW(UK) SS | 2.0 | | | | | | | | |
| 8 HOW OLD | 1.6 | 75191.0 | 39045.0 | 37534.0 | 37770.0 | 47385.0 | 16064.1 | 37534.0 | 79.2 |
| 9 HOW 280 | 1.6 | 203230.0 | 136272.0 | 241816.0 | 264744.0 | 211515.5 | 48686.8 | 136272.0 | 64.4 |
| 10 ACUMED | 1.6 | 55822.0 | 51532.0 | 38143.0 | 63091.0 | 52147.0 | 9079.7 | 38143.0 | 73.1 |
| 11 BIODYNAMICS | 1.6 | 64784.0 | 61182.0 | 55291.0 | 38571.0 | 54957.0 | 10049.0 | 38571.0 | 70.2 |
| 12 ZIMMER CrCo | 1.6 | 1450605.0* | 1017006.0* | 1024842.0* | 1000164.0* | 1123154.3 | 189263.9 | 1000164.0 | 89.0 |
| 13 ZIMMER Ti | 1.6 | 22178.0 | 23446.0 | 26251.0 | 31698.0 | 25893.3 | 3661.1 | 22178.0 | 85.7 |
| 14 HOW(USA) SS | 1.6 | 80594.0 | 120056.0 | 97107.0 | 107570.0 | 101331.8 | 14469.1 | 80594.0 | 79.5 |
| 15 HOW(UK) SS | 1.6 | | | | | | | | |
| 16 RICHARDS | 1.2 | 8257.0 | 13327.0 | 11499.0 | 10206.0 | 10822.3 | 1850.1 | 8257.0 | 76.3 |

TEST CONDITIONS:
LOADS: 500 N FOR ALL 1.6 mm CABLES AND 880 N FOR ALL 2.0 mm CABLES
FREQUENCY: 10 Hz FOR ALL TESTS.
* SPECIMEN HAD A RUN-OUT, NO FAILURE OCCURRED.

FIG.23

ORTHOPAEDIC WIRES AND CABLES AND METHODS OF MAKING SAME

BACKGROUND OF THE INVENTION

1. Field of the Invention

The invention relates to orthopaedic wires and cables which have an improved resistance to failure over prior art wires and cables; and to methods for making such wires and cables.

2. Description of the Related Art

Multifilament cables and monofilament wires are used in a variety of orthopaedic applications. The cables and wires are typically made of stainless steel, titanium, or a cobalt-chromium alloy.

Multifilament cable generally provides superior fixation in trochanteric reattachment procedures. In addition, these cables perform exceptionally well, not only for trochanteric reattachment, but also for a wide variety of reconstructive and trauma applications. Many surgeons use cable for reduction and fixation of fractures of the femur, patella, humerus, and other bones. Cables are also used prophylactically for prevention of fractures in primary or revision total hip surgery.

In order for either wire or cable to perform well in clinical applications, it must possess certain properties. Cable manufacturers generally consider tensile strength to be the primary measure of wire and cable strength and the most important factor for clinical applications.

Wire is manufactured from forget billets using a rolling mill and a drawing bench. The preliminary treatment of the material to be manufactured into wire is done in the rolling mill where hot billets are rolled to round wire rod. The action of atmospheric oxygen causes a coating of mill scale to form on the hot surface of the rod and must be removed. This descaling can be done by various mechanical methods (e.g., shot-blasting) or by pickling, i.e., immersion of the wire rod in a bath of dilute sulphuric or hydrochloric acid. After pickling, the wire rod may additionally undergo a jolting treatment which dislodges the scale loosened by the acid. The remaining acid is removed by immersion of the wire rod in lime water.

The actual process of forming the wire is called drawing and is carried out on the metal in a cold state with a drawing bench. Prior art FIG. 1 shows a simple drawing bench 10. The wire 12 is pulled through a draw plate 14 which is provided with a number of holes, e.g. 16, (dies) of various diameters. These dies have holes which taper from the diameter of the wire 12 that enters the die to the smaller diameter of the wire 12' that emerges from the die. The thick wire rod 12 is coiled on a vertical spool 18 called a swift and is pulled through the die by a rotating drum 20 mounted on a vertical shaft 22 which is driven by bevel gearing 24. The drum can be disconnected from the drive by means of a clutch 26. To pass a wire through a die, the end of the wire is sharpened to a point and threaded through the die. It is seized by a gripping device and rapidly pulled through the die. This is assisted by lubrication of the wire. Each passage through a die reduces the diameter of the wire by a certain amount. By successively passing the wire through dies of smaller and smaller diameter, thinner and thinner wire is obtained. The dies used in the modern wire industry are precision-made tools, usually made of tungsten carbide for larger sizes or diamond for smaller sizes. The die design and fabrication is relatively complex and dies may be made of a variety of materials including single crystal natural or synthetic diamond, polycrystalline diamond or a mix of tungsten and cobalt powder mixed together and cold pressed into the carbide nib shape.

A cross section of die 16 is shown in prior art FIG. 2. Generally, the dies used for drawing wire have an outer steel casing 30 and an inner nib 32 which, as mentioned above, may be made of carbide or diamond or the like. The die has a large diameter entrance 34, known as the bell, which is shaped so that wire entering the die will draw lubricant with it. The shape of the bell causes the hydrostatic pressure to increase and promotes the flow of lubricant into the die. The region 36 of the die where the actual reduction in diameter occurs is called the approach angle. In the design of dies, the approach angle is an important parameter. The region 38 following the approach angle is called the bearing region. The bearing region does not cause diametric reduction, but does produce a frictional drag on the wire. The chief function of the bearing region 38 is to permit the conical approach surface 36 to be refinished (to remove surface damage due to die wear) without changing the die exit. The last region 40 of the die is called the back relief. The back relief allows the metal wire to expand slightly as the wire leaves the die. It also minimizes the possibility of abrasion taking place if the drawing stops or if the die is out of alignment with the path of the wire.

Although wire drawing appears to be a simple metalworking process, those skilled in the art will appreciate that many different parameters affect the physical quality of the drawn wire. Among these parameters, draw stress and flow stress play an important role. A discussion of the practical aspects wire drawing can be found in Wright, Roger N., "Mechanical Analysis and Die Design", Wire Journal, October 1979, the complete disclosure of which is hereby incorporated by reference herein.

Cable is manufactured by twisting multiple strands (filaments) of wire together. The material properties of cable are related to the material properties of the individual wire filaments which make up the cable. When considering the strength of multifilament cables, material strength expressed as stress only applies to the strength of individual cable filaments. Overall cable strength must be measured in terms of the actual load-carrying capacity of the cable. Cable strength is therefore be a function of two variables: the filament material strength and the cable construction. Improved cable strength can be achieved by increasing filament material strength, modifying cable construction, or both.

Other wire and cable properties include the following: ductility, a measure of the plastic deformation a cable or wire can withstand before fracturing; fatigue strength, a cable's ability to resist fracture under cyclic loading conditions; material toughness, the material's ability to absorb energy and resist fracture while under going plastic (non-reversible) deformation; ultimate tensile strength, the maximum stress achieved in a material before fracture occurs; and yield strength, the stress above which plastic (non-reversible) deformation of a material occurs.

As mentioned above, manufacturers of orthopaedic wires and cables generally consider ultimate tensile strength to be the most important property and have endeavored to provide cables and wires with very high tensile strength. Despite these efforts, clinical experience shows that even high tensile strength cables and wires can fail by fracture.

SUMMARY OF THE INVENTION

It is therefore an object of the invention to provide orthopaedic cables and wires which are resistant to failure.

It is also an object of the invention to provide methods for making orthopaedic cables and wires which are resistant to failure.

In accord with these objects which will be discussed in detail below, the wires, cables, and methods of the present invention are based on the discovery that, in clinical orthopaedic applications, material toughness and fatigue strength are as important or more important than ultimate tensile strength.

By analysis of clinically retrieved fractured cables and laboratory testing of cables having different tensile strengths, it was found that the failure resistance of high tensile strength cable is actually improved by reducing its tensile strength. The analyses and tests revealed that reducing tensile strength resulted in increasing material toughness and fatigue strength. The tests showed that the dynamic stresses (associated with fatigue strength) placed on cables and wires in orthopaedic applications were as important or more important than the static stresses (associated with tensile strength). Fractographic analysis of clinically retrieved cables revealed that cable fracture is initiated by fatigue and not by tensile overloading. It was found that a fatigue fracture occurs when a material is subjected to cyclic or fluctuating stresses. Under this repetitive loading, a small crack forms in the material and propagates with each loading cycle until final fracture occurs. The tests revealed that the stress which causes a fatigue failure is normally much less than the ultimate tensile strength of the material.

Experiments were performed to determine the effects of annealing and cold working on the tensile strength and fatigue strength of orthopaedic cables. The experiments revealed that the hardness and tensile strength of the cables were reduced by annealing, but that annealing improved the fatigue strength of the cables. It was also found that by starting with a relatively high tensile strength cable, annealing would increase fatigue strength.

Other experiments revealed that fatigue strength is improved by reducing the amount of cold working which normally increases tensile strength.

Cable fabricated from filaments having an ultimate tensile strength equal to or less than 175 ksi had more than a six fold increase in cable fatigue life as compared to cable fabricated from filaments having an ultimate tensile strength of 280 ksi. Cold working of fully annealed wire to decrease the diameter of the wire by approximately 18% resulted in wires having the an improved combination of tensile strength and fatigue strength over prior art cables. The presently preferred cables and wires according to the invention are made from wrought VITALLIUM (registered trademark) cobalt-chromium alloy.

Additional objects and advantages of the invention will become apparent to those skilled in the art upon reference to the detailed description taken in conjunction with the provided figures.

BRIEF DESCRIPTION OF THE DRAWINGS

FIG. 22 is Table 4 which shows the results of tensile strength tests on a number of cables tested;

FIG. 23 is Table 5 which shows the results of fatigue strength tests on a number of cables tested;

DETAILED DESCRIPTION

Failure analyses of clinically retrieved and laboratory fatigue tested cables suggests that the fatigue strength of the cables can be improved by reducing the tensile strength.

The high tensile strength of wrought VITALLIUM (registered trademark) alloy wire is achieved by high plastic deformation at room temperature (cold working). The failure analyses suggested that less cold working may improve the fatigue strength and ductility of wrought VITALLIUM (registered trademark) alloy cable.

Three phases of experiments were conducted in order to test these hypotheses. In the first phase, experiments were conducted to determine the effects of annealing on the strength, microstructure, and hardness of a high strength wrought VITALLIUM (registered trademark) alloy cable.

As a result of these experiments, a cable which had been annealed to reduce its tensile strength to 210–240 ksi was selected for further fatigue testing. In the second phase, experiments were conducted to measure the fatigue strength and to analyze the fracture surface of annealed cables after fatigue testing. The third phase included experiments designed to determine the optimum combination of tensile strength and fatigue strength.

Following the annealing tests, cables were formed from filaments which were fully annealed and then cold worked to produce the desired tensile strength.

First Phase Experiments

Nine 1.6 mm wrought VITALLIUM (registered trademark) alloy cables were used in the experiments. The cables had a breaking strength of approximately 413 lbs. and the ultimate tensile strength of the individual filaments in the cables was approximately 309–340 ksi.

Metallography Tests

Eight cables were ultrasonically cleaned with acetone for 10 minutes and then dried in air prior to vacuum annealing. Each cable was annealed at a different temperature for 15 minutes followed by nitrogen quench. In particular, the eight cables were annealed at 1050 degrees F, 1250 degrees F, 1550 degrees F, 1650 degrees F, 1750 degrees F, 1850 degrees F, 1950 degrees F and 2050 degrees F, respectively.

Figure 1:
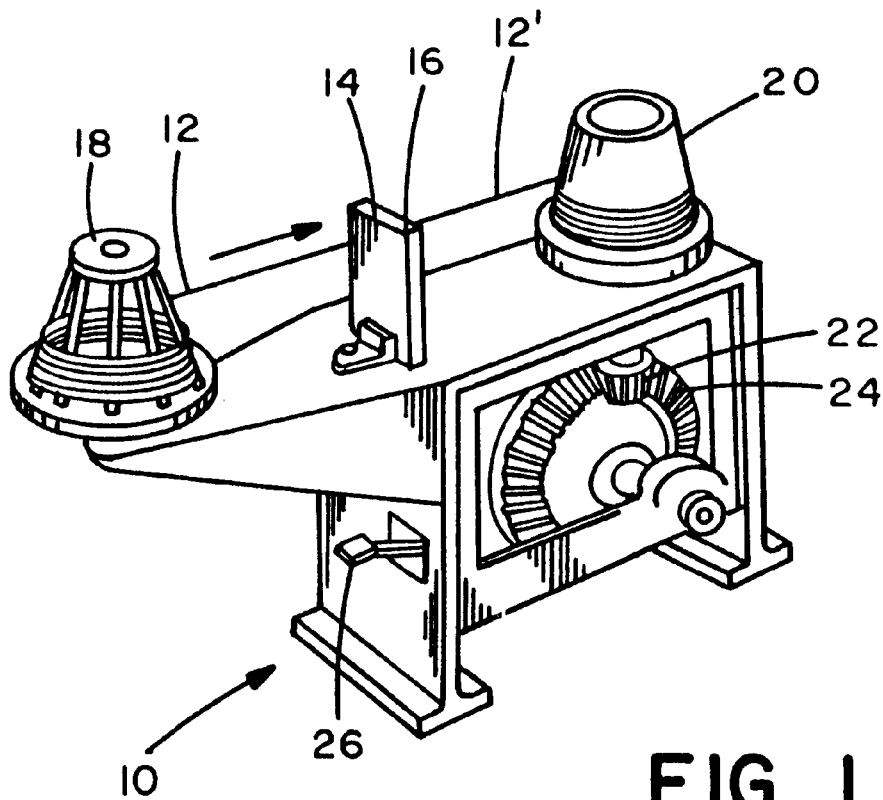
FIG. 1 is perspective view of a prior art wire drawing bench.
Figure 2:
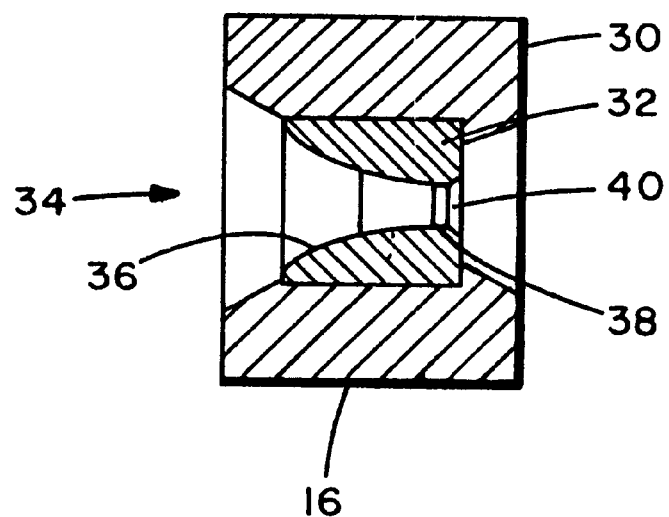
FIG. 2 is a cross sectional view of a prior art wire forming die.

The ninth (untreated) cable and the annealed cables were mounted to observe the cross section of individual wires (filiments) of the cable for metallographic examination and hardness measurements. In particular, each cable was mounted in Epomet molding compound and ground with successively finer silicon carbide paper to 1200 grit, then polished. Electrolytical etching at 3 volts for approximately 2 to 3 seconds in a 97% HCl+3% H202 (30% concentration) solution was used to reveal the microstructure. FIGS. 1–9 show the microstructures of an individual filament in each of the nine cables. FIG. 1 shows the microstructure of a filament in the untreated cable and FIGS. 2–9 show the microstructures of filaments in the annealed cables.

Figure 3:
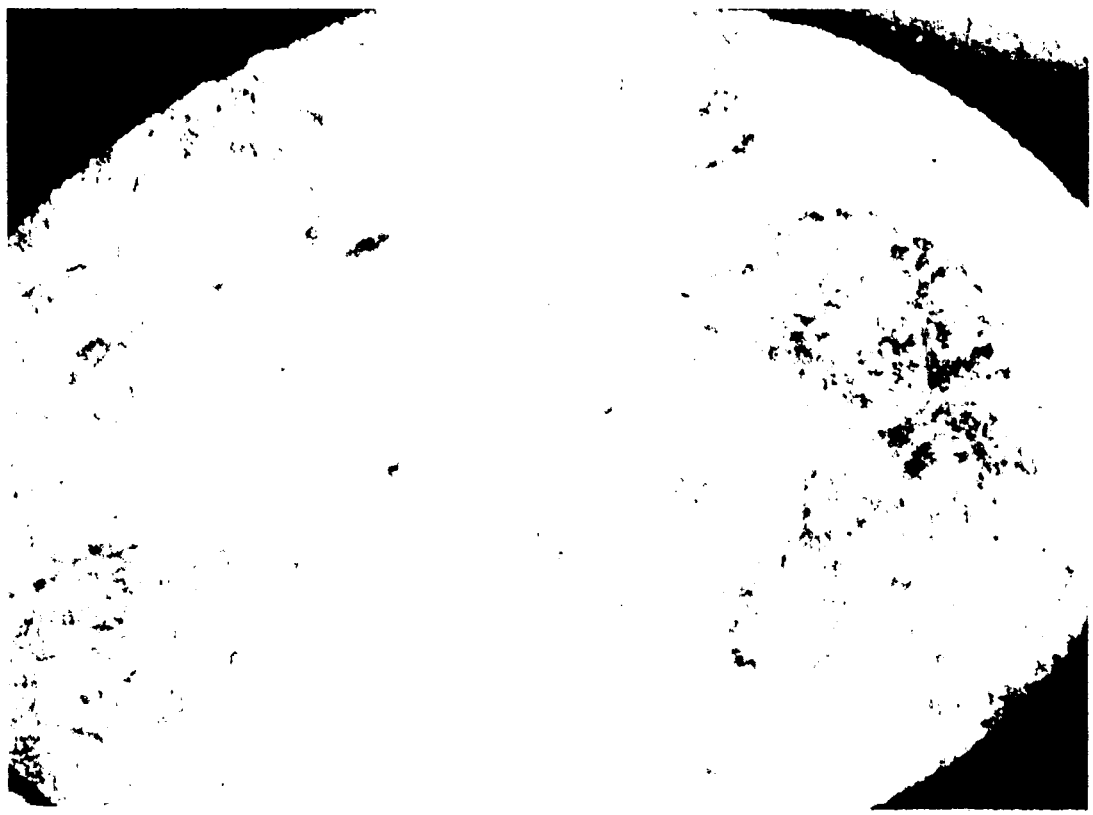
FIG. 3 is a micrograph of the microstructure of one filiment of a 1.6 mm wrought VITALLIUM (registered trademark) alloy cable.
Figure 4:
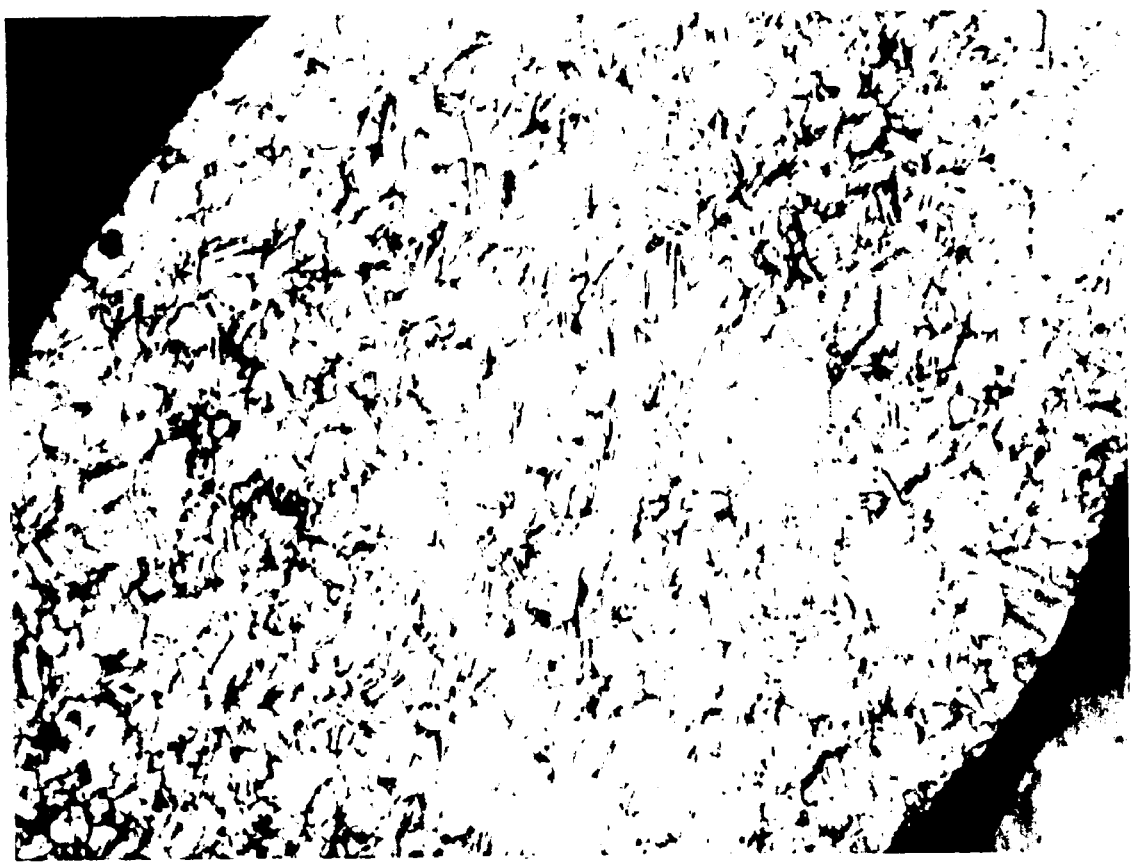
FIG. 4 is a micrograph of the microstructure of one filiment of a 1.6 mm wrought VITALLIUM (registered trademark) alloy cable after annealing at 1050 degrees F.
Figure 5:
FIG. 5 is a micrograph of the microstructure of one filiment of a 1.6 mm wrought VITALLIUM (registered trademark) alloy cable after annealing at 1250 degrees F.
Figure 6:
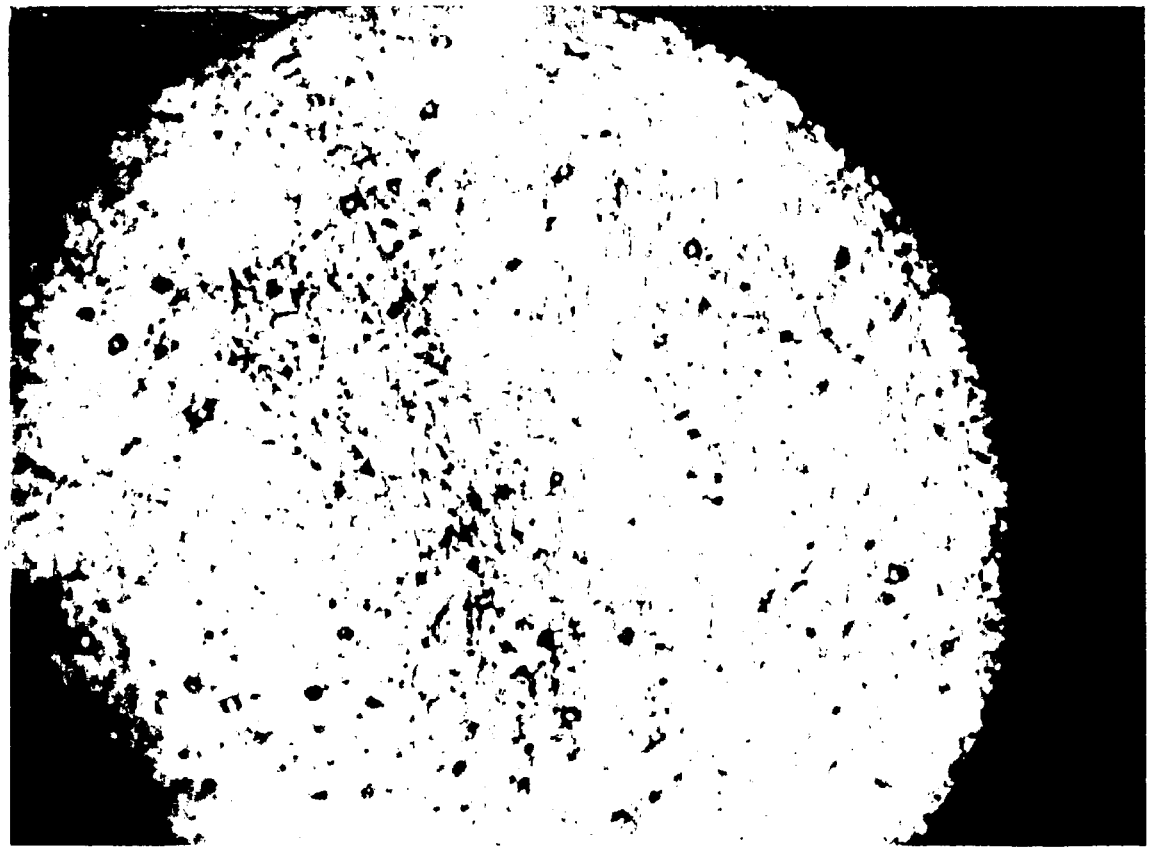
FIG. 6 is a micrograph of the microstructure of one filiment of a 1.6 mm wrought VITALLIUM (registered trademark) alloy cable after annealing at 1550 degrees F.
Figure 7:
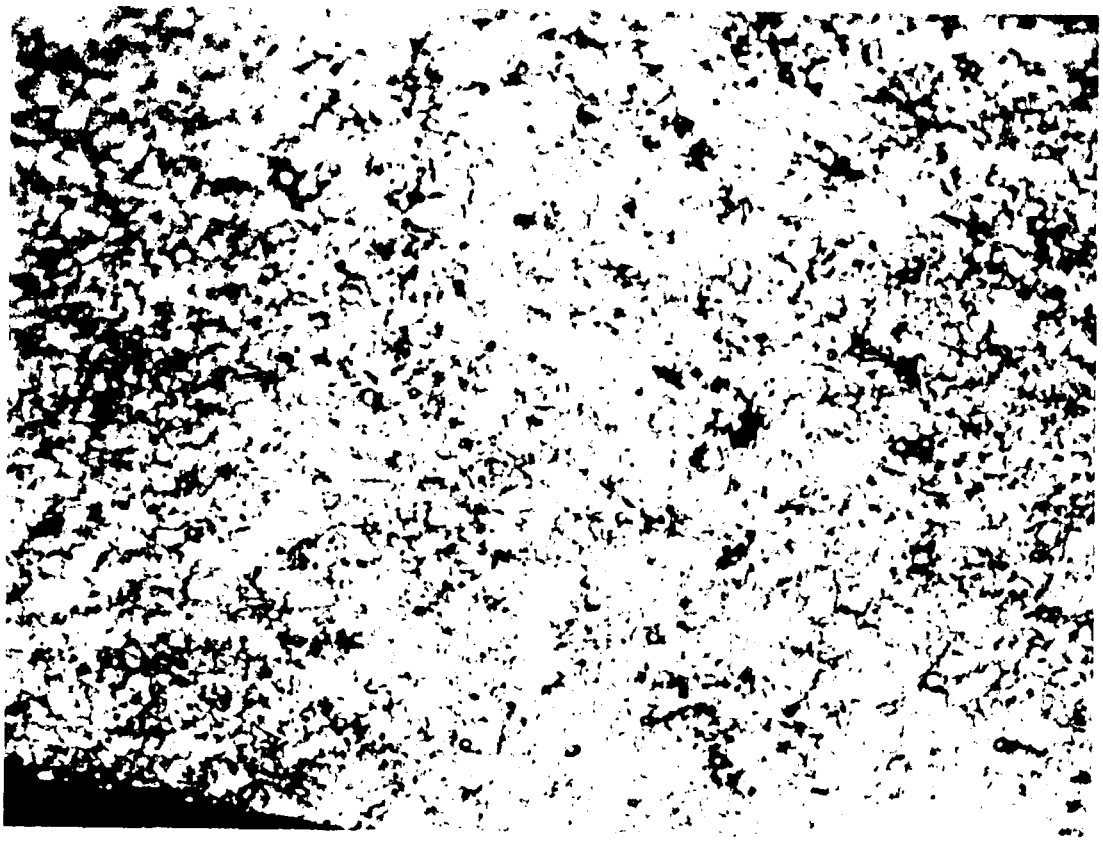
FIG. 7 is a micrograph of the microstructure of one filiment of a 1.6 mm wrought VITALLIUM (registered trademark) alloy cable after annealing at 1650 degrees F.
Figure 8:
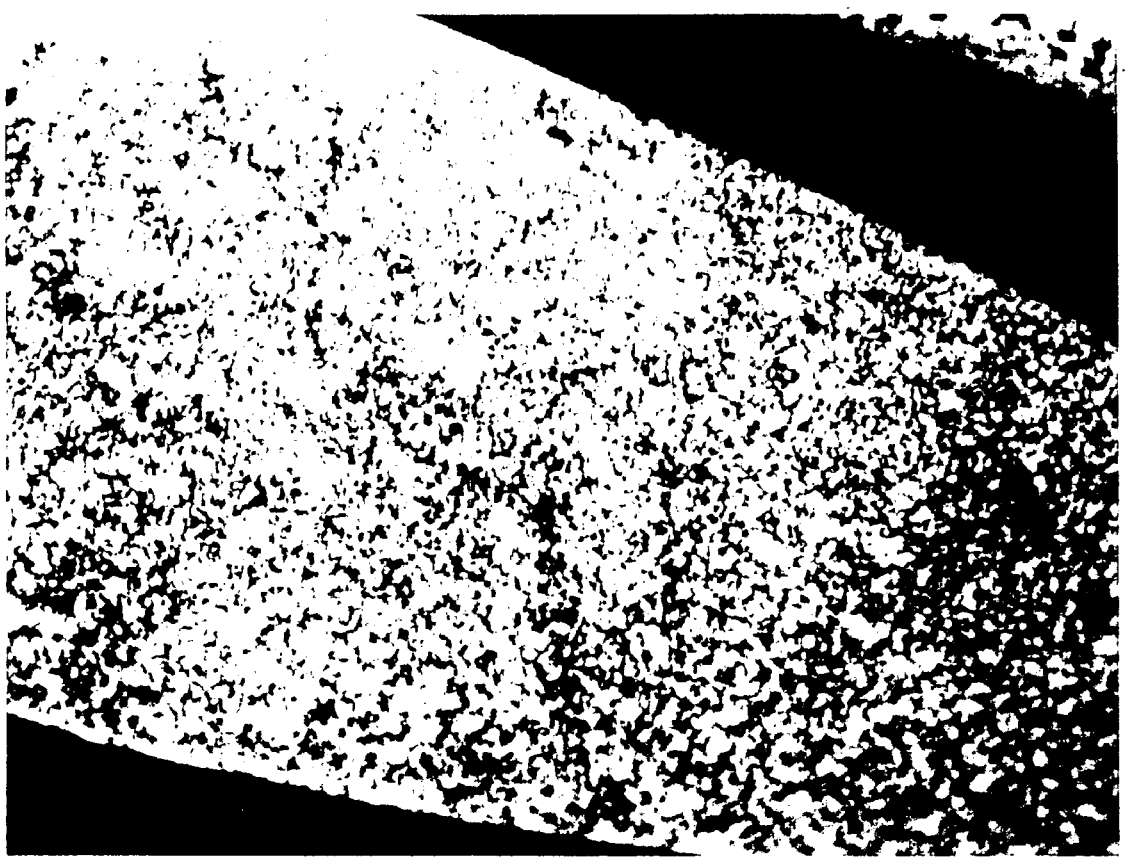
FIG. 8 is a micrograph of the microstructure of one filiment of a 1.6 mm wrought VITALLIUM (registered trademark) alloy cable after annealing at 1750 degrees F.
Figure 9:
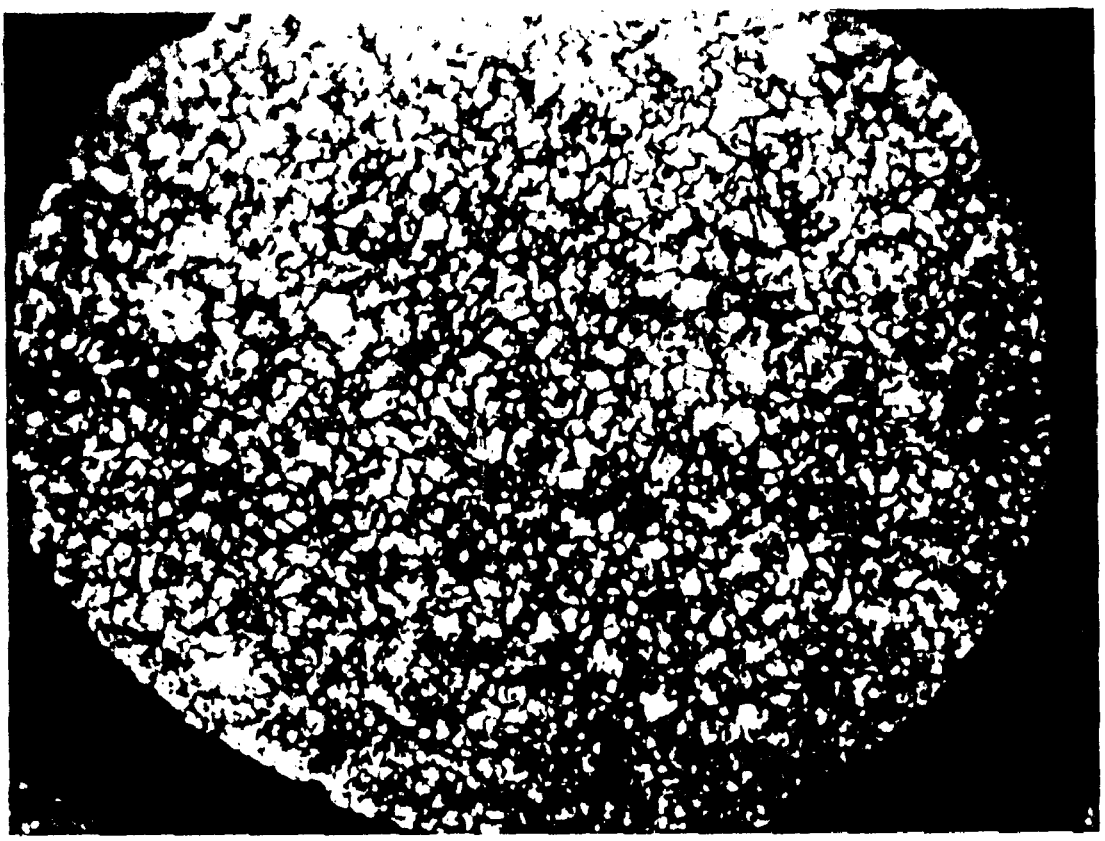
FIG. 9 is a micrograph of the microstructure of one filiment of a 1.6 mm wrought VITALLIUM (registered trademark) alloy cable after annealing at 1850 degrees F.
Figure 10:
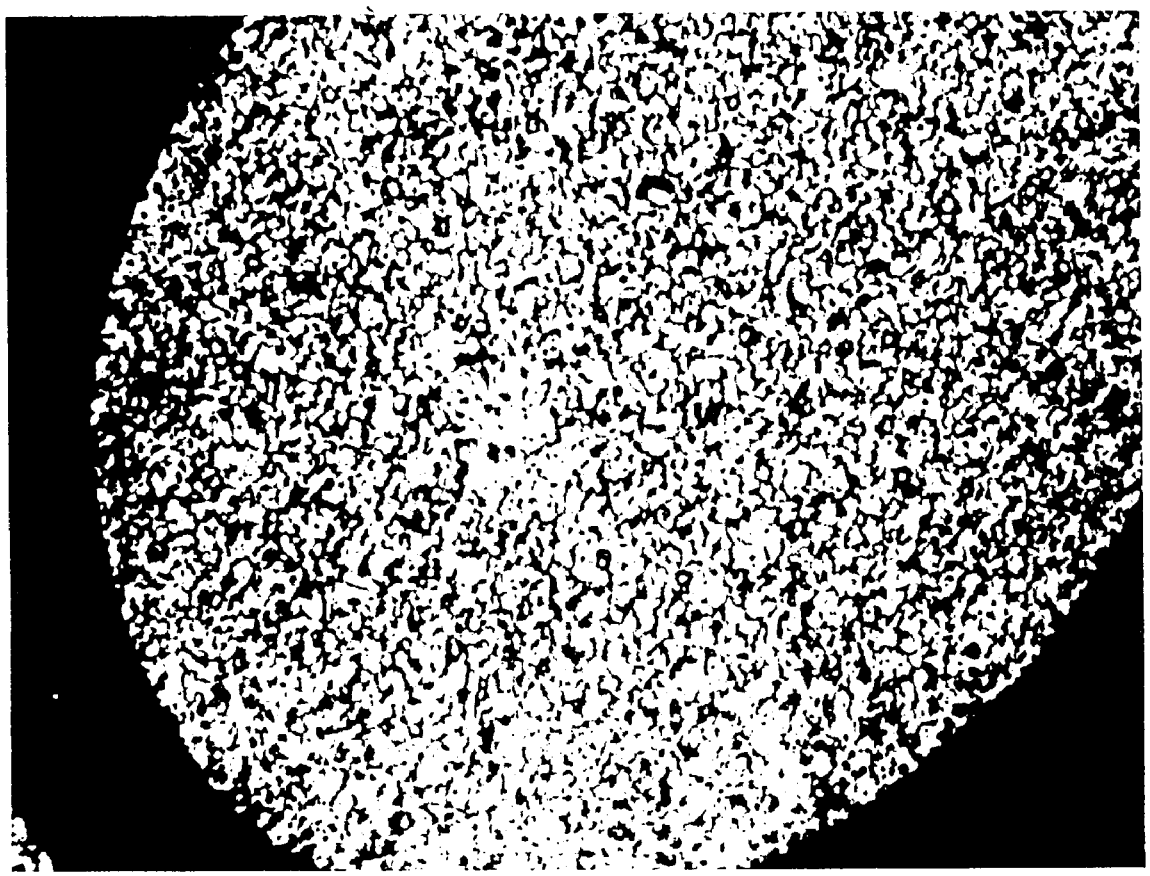
FIG. 10 is a micrograph of the microstructure of one filiment of a 1.6 mm wrought VITALLIUM (registered trademark) alloy cable after annealing at 1950 degrees F.
Figure 11:
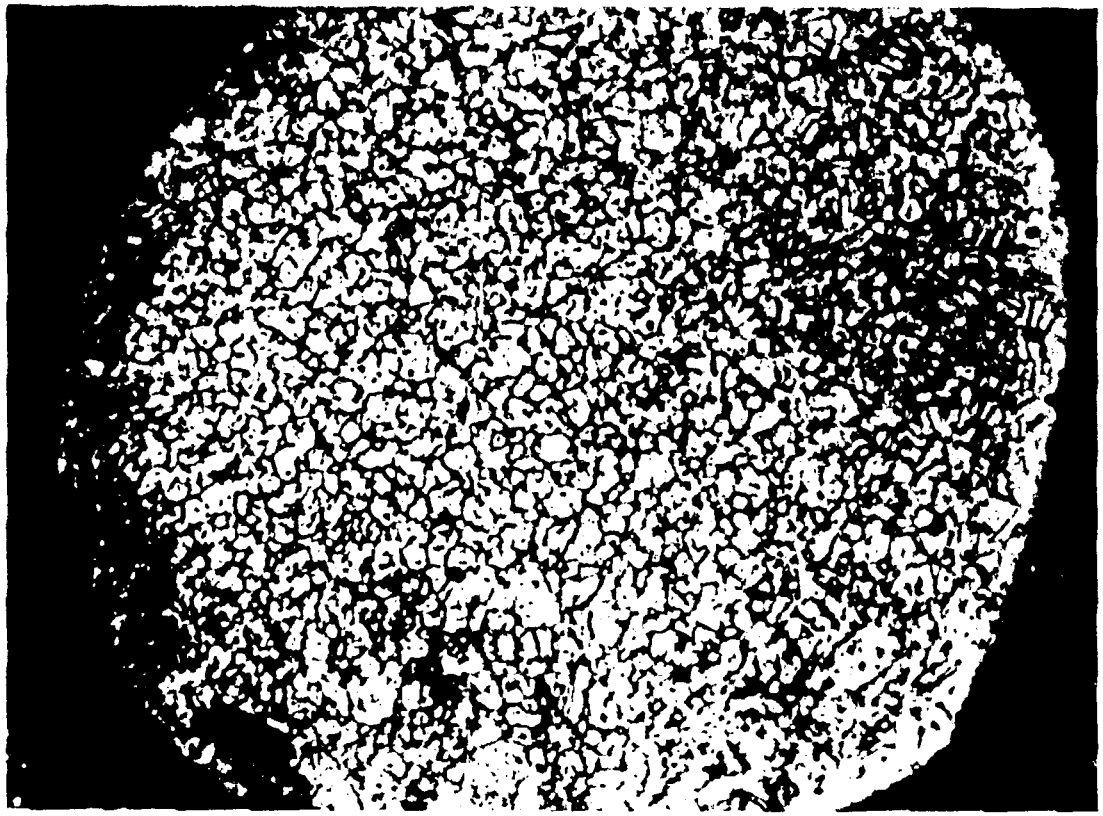
FIG. 11 is a micrograph of the microstructure of one filiment of a 1.6 mm wrought VITALLIUM (registered trademark) alloy cable after annealing at 2050 degrees F.

Referring now to FIGS. 3–11, the cable without annealing exhibited a heavily cold deformed grain structure as shown in FIG. 3. As shown in FIGS. 4 and 5, deformation bands were still present after annealing at 1050 degrees F and 1250 degrees F. Formation of nuclei was visible in the cable annealed at 1550 degrees F as shown in FIG. 6. After annealing at 1850 degrees or 1950 degrees F, completely recrystallized grains were formed as shown in FIGS. 9 and 10. Grain growth was observed in the cable annealed at 2050 degrees F as shown in FIG. 11.

Hardness Tests

In addition to examining the microstructures of the cables, Knoop hardness measurements of the polished cables were recorded at a 500 gram load using a LECO-400 microhardness tester. The results of the hardness tests (converted to the Rockwell C scale) are shown in Table 1, below.

TABLE 1

| Cable | Hardness Measurements (Rockwell c) | | | | Average |
| --- | --- | --- | --- | --- | --- |
| Untreated | 56.0 | 57.5 | 57.5 | 57.5 | 57 |
| 1050 deg. F. | 56.0 | 55.0 | 52.5 | 54.0 | 55 |
| 1250 deg. F. | 48.5 | 50.0 | 49.5 | 52.0 | 50 |
| 1550 deg. F. | 49.0 | 47.0 | 47.0 | 48.5 | 48 |
| 1650 deg. F. | 45.5 | 45.5 | 45.5 | 46.0 | 46 |
| 1750 deg. F. | 42.5 | 43.5 | 43.5 | 43.0 | 43 |
| 1850 deg. F. | 41.5 | 41.5 | 41.0 | 40.0 | 41 |

TABLE 1-continued

| Cable | Hardness Measurements (Rockwell c) | | | | Average |
| --- | --- | --- | --- | --- | --- |
| 1950 deg. F. | 43.0 | 41.0 | 40.0 | 40.0 | 41 |
| 2050 deg. F. | 33.0 | 36.0 | 32.5 | 36.0 | 34 |

From the hardness tests it was confirmed that the hardness of high strength wrought VITALLIUM (registered trademark) alloy cable deceases with increasing annealing temperature. The hardness of the 1.6 mm cable before annealing was Rc 57. A 15-minute anneal at 2050 degrees F lowered the hardness from Rc 57 to Rc 34. In general, an alloy having higher hardness exhibits higher tensile strength and lower ductility.

Tensile Strength Tests

Four of the annealed cables (1550, 1750, 1950, and 2050 degrees F) and the untreated cable were pull tested to determine the effects of annealing on cable strength. The pull test is a standard test to measure the breaking strength of a cable. The results of the pull tests are shown in Table 2, below, which also shows the hardness of all of the cables for reference. The tensile strength of the filaments is calculated from the pull test load and the cross sectional area of individual filaments. The hardness and tensile strength of a fully annealed cable is also shown in Table 2 for reference. The "Untreated" row of the table contains actual test data; the other rows contain estimates.

TABLE 2

| Cable | Hardness (Rc) | Cable Pull Test Load (lbs.) | Filiment Tensile strength (Ksi) |
| --- | --- | --- | --- |
| Untreated | 57 | 413 | 309–340 |
| 1050 deg. F. | 55 | — | — |
| 1250 deg. F. | 50 | — | — |
| 1550 deg. F. | 48 | 304–313 | 230–255 |
| 1650 deg. F. | 46 | — | — |
| 1750 deg. F. | 43 | 294–307 | 225–245 |
| 1850 deg. F. | 41 | — | — |
| 1950 deg. F. | 41 | 282 | 210–240 |
| 2050 deg. F. | 34 | 245 | 180–200 |
| Fully Annealed | 20 | — | 67 |

As shown in Table 2, the cables annealed at higher temperatures exhibited lower breaking strength (and lower tensile strength of the filaments). The breaking strength of untreated 1.6 mm cable reduced from 413 lbs to 245 lbs after annealing at 2050 degrees F for 15 minutes. Table 2 also shows the hardness and tensile strength of a production run of fully annealed wrought VITALLIUM (registered trademark) alloy cable which was produced by annealing at 2160 degrees F at 175 feet per minute.

From the first phase experiments, it was demonstrated that the tensile strength and the hardness of wrought VITALLIUM (registered trademark) alloy cables decreased with annealing and that higher annealing temperatures resulted in greater decreases in hardness and tensile strength. Cables annealed at 1850–1950 degrees F exhibited a completely recrystallized grain structure. It was hypothesized that these cables would posses improved fatigue strength as compared to the untreated wrought VITALLIUM (registered trademark) alloy cables while still retaining sufficent tensile strength.

Second Phase Experiments

Three 1.6 mm wrought VITALLIUM (registered trademark) alloy cables were ultrasonically cleaned with acetone for 10 minutes and dried in air prior to vacuum annealing at 1950 degrees F for 15 minutes. It was unknown whether the three cable specimens were from the same lot. Therefore, the ultimate tensile strength of the filaments in the different cables may have varied from about 309 to 340 ksi before annealing.

Fatigue Tests

Figure 12:
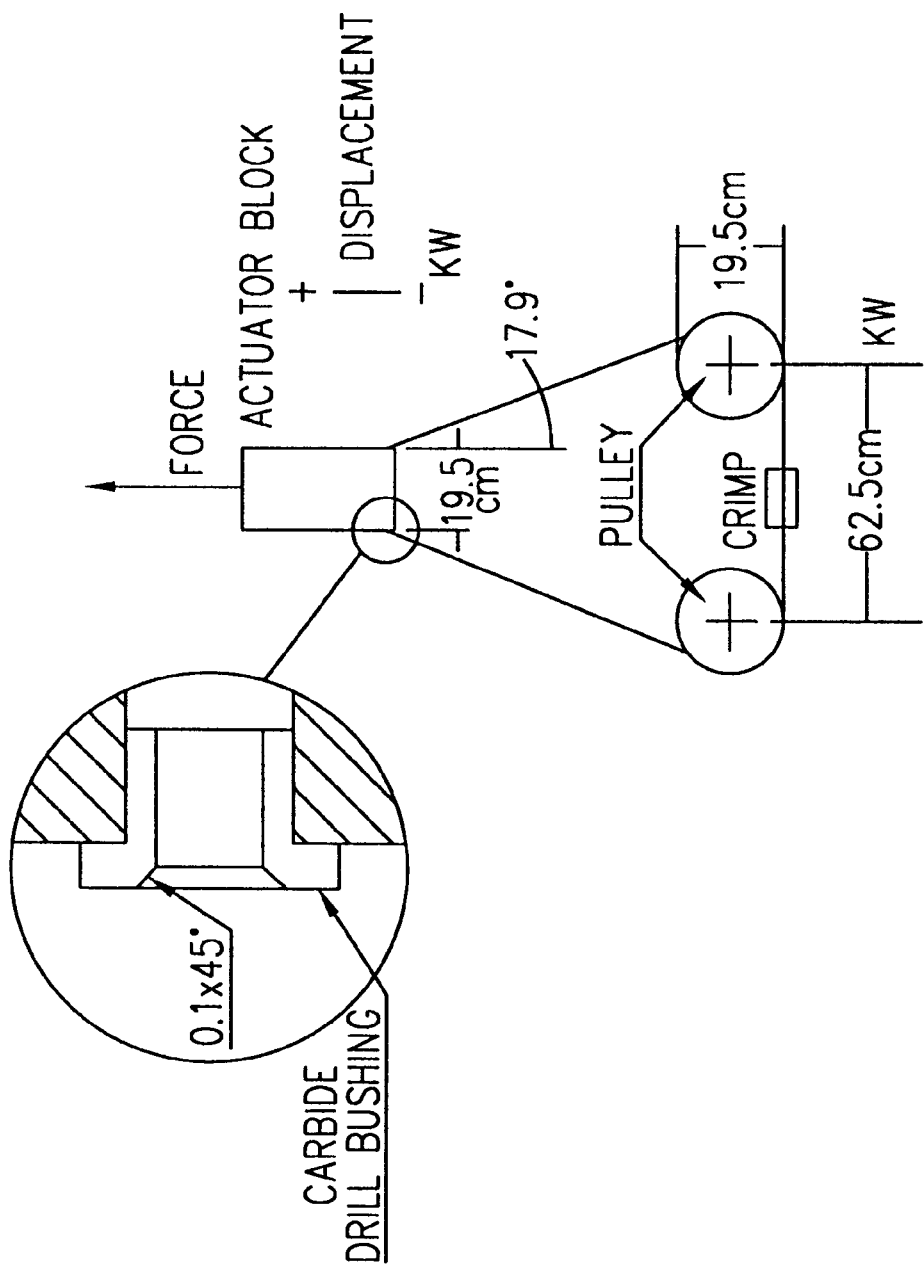
FIG. 12 is a schematic diagram of an apparatus used to test fatigue strength.

The three annealed cables and several untreated cables were subjected to fatigue testing. Fatigue tests were performed on a servo-hydraulic Instron machine (Model 8521). A schematic diagram of the fatigue test set-up is shown in FIG. 12. The cable specimens were crimped between the two pulleys. All three annealed cables were tested at 500 N at a frequency of 10 Hz. Tests were run to 1,000,000 cycles or to failure, whichever occurred first.

The fatigue strength of 1950 degrees F annealed cables clearly exceeded that of the untreated cables. The annealed cables tested at a force of 500 N had cycles to failure of 439,039 to over 1,000,000 cycles. The untreated high tensile strength cables failed after 11,169 to 24,798 cycles.

Metallography Tests

The untreated and the annealed cables were examined after failure using a Phillips XL-40 scanning electron microscope (SEM) to determine the fracture mode.

Figure 13:
FIG. 13 is a scanning electron microscope fractograph of an untreated cable after fatigue failure.
Figure 14:
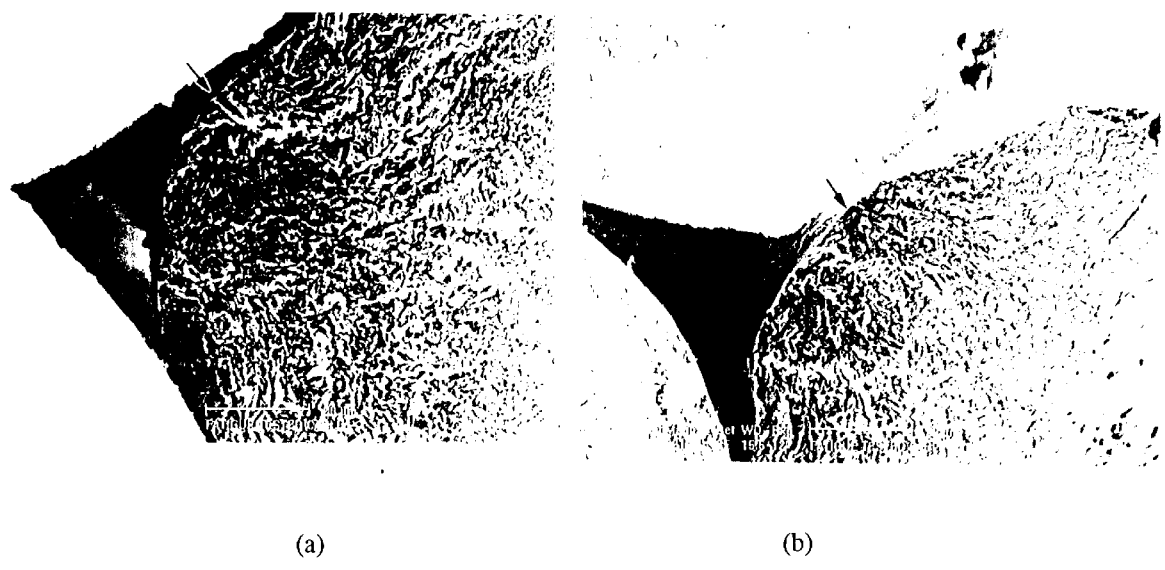
FIGS. 14a and 14b are higher magnification views of the wires of the cable shown in FIG. 13.
Figure 15:
FIG. 15 is a scanning electron microscope fractograph of an annealed cable after fatigue failure.
Figure 16:
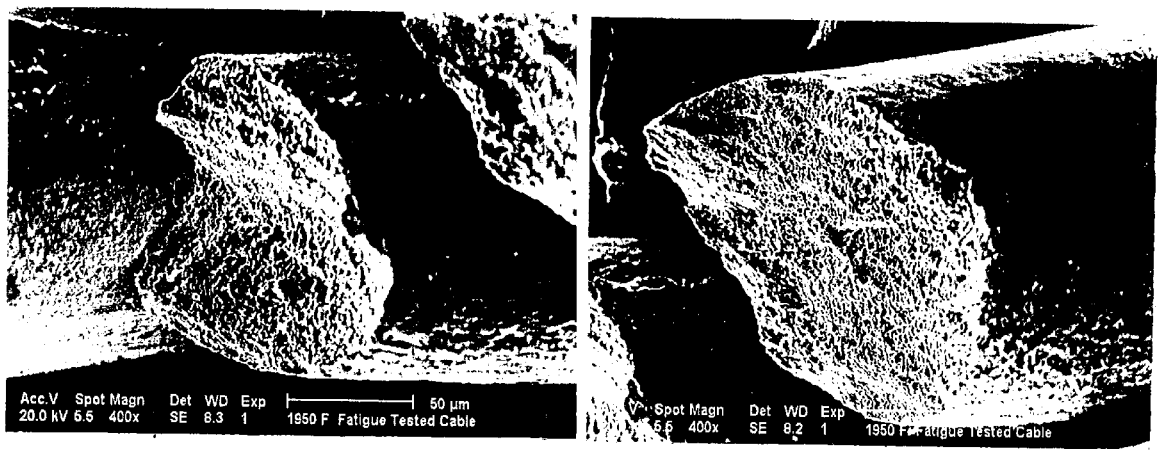
FIGS. 16a and 16b are higher magnification views of the wires of the cable shown in FIG. 15.

As shown in FIGS. 13, 14a, and 14b, the untreated cable was found to be notch sensitive. Fatigue cracks initiated at contact points of wires where high stress concentration occurred. The radiated chevron marks in FIGS. 14a and 14b indicate the location of fracture initiation (FIG. 14a shows a higher magnification view of the wire marked 1 in FIG. 13; FIG. 14b shows a higher magnification view of the wire marked 2 in FIG. 13). SEM analysis on the fracture surface of the annealed cables after fatigue testing revealed that the annealed cable was much less notch sensitive than the untreated cables. There were no signs of fatigue fracture initiation at the contact points of the annealed wires. Ductile dimples indicating the cable to be relatively ductile were noted on the fracture surface of annealed cables as shown in FIGS. 15, 16a, and 16b (FIG. 16a shows a higher magnification view of the wire marked 1 in FIG. 15; FIG. 16b shows a higher magnification view of the wire marked 2 in FIG. 15).

The second phase experiments showed that the annealed lowered tensile strength cables have a better fatigue strength than the high tensile strength untreated cables.

Third Phase Experiments

Two prototype lots of annealed wrought VITALLIUM (registered trademark) alloy cables were evaluated. One lot (1.6 and 2.0 mm) was manufactured from wire having an ultimate tensile strength of 280 ksi. The other lot (2.0 mm) was produced from wires having an ultimate tensile strength of 175 ksi. It was reported that the two prototype cables were the homogeneous cable construction, i.e. all filaments are the same size. This construction was different from that of the original high strength cables, i.e. center filament is a different size from the outer filaments. For comparison, a number of other commercially available Cr—Co alloy cables were tested and a number of commercially available stainless steel and titanium cables were tested.

Metallography and Hardness Tests

Metallography and hardness measurement were conducted on the prototype cables and the comparison cables. The same polishing and etching methods were used as in the first phase experiments. The hardness was measured using a LECO-400 microhardness tester. Table 3, below, shows the results of the hardness tests.

TABLE 3

| Specimen | Hardness |
| --- | --- |
| Untreated VITALLIUM (Reg. TM) | Rc 57 |
| VITALLIUM (Reg. TM) Prototype (280 ksi) | Rc 58 |
| VITALLIUM (Reg. TM) Prototype (175 ksi) | Rc 38 |
| Acumed Cr—Co Alloy | Rc 56 |
| Zimmer Cr—Co Alloy | Rc 30 |
| Biodynamics Cr—Co Alloy | Rc 60 |

The hardness of 280 ksi cables was measured to be Rc 58 which was comparable to that of the untreated (309–340 ksi) cable. The hardness of 175 ksi prototype cable was Rc 38, lower than that of 1950 degrees F annealed cable produced in the first phase experiments. The hardness of Acumed and Biodynamics cable was comparable to that of untreated wrought VITALLIUM (registered trademark) alloy cable. The hardness of Zimmer cable was Rc 30, lower than that of the 175 ksi prototype cable (Rc 38).

Figure 17:
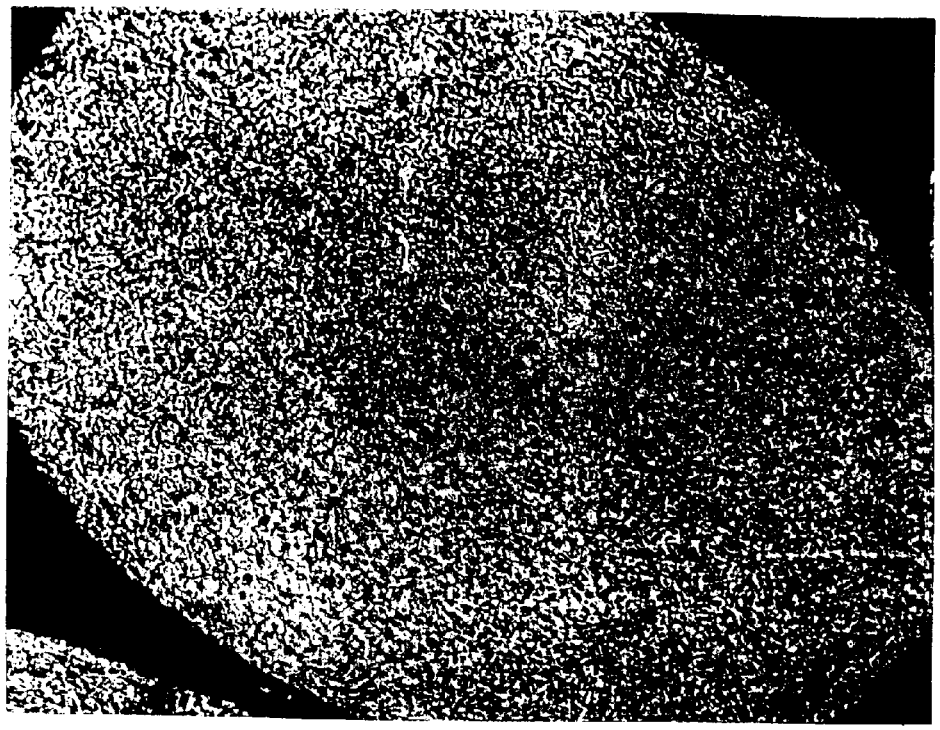
FIG. 17 is a micrograph of the microstructure of a 280 ksi prototype wrought VITALLIUM (registered trademark) alloy cable.
Figure 18:
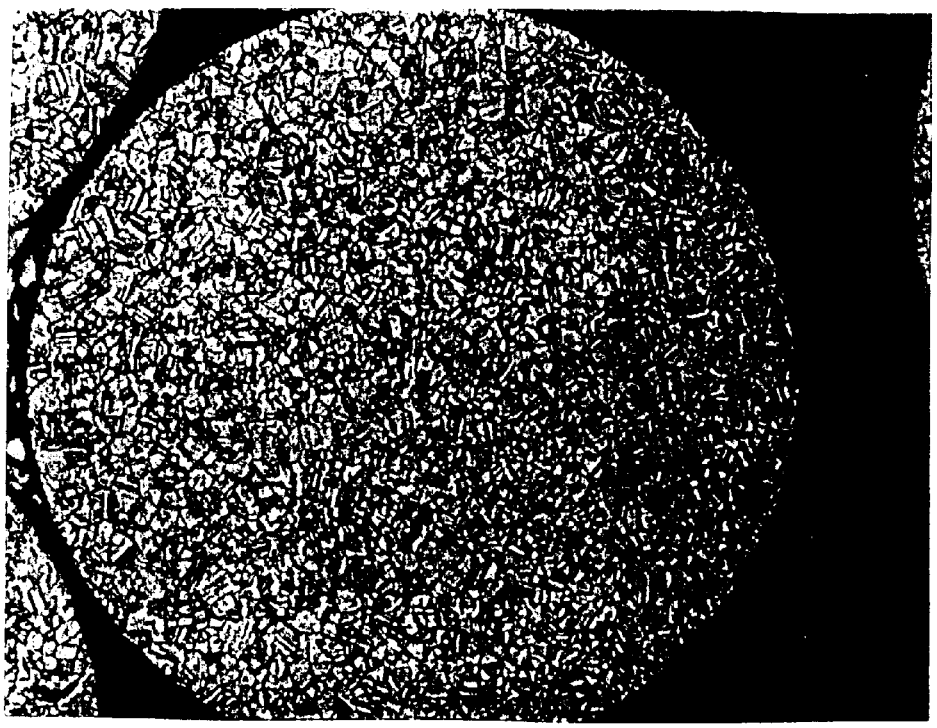
FIG. 18 is a micrograph of the microstructure of a 175 ksi prototype wrought VITALLIUM (registered trademark) alloy cable.

Typical microstructures of the 280 and 175 ksi prototype cables are shown in FIGS. 17 and 18 respectively. The 280 ksi cable exhibited a heavily deformed grain structure, similar to that of the untreated wrought VITALLIUM (registered trademark) alloy cables (309–340 ksi). The 175 ksi cable showed a fully recrystallized grain structure. Small grain growth (ASTM #10 or finer) was also noted in FIG. 18.

Figure 19:
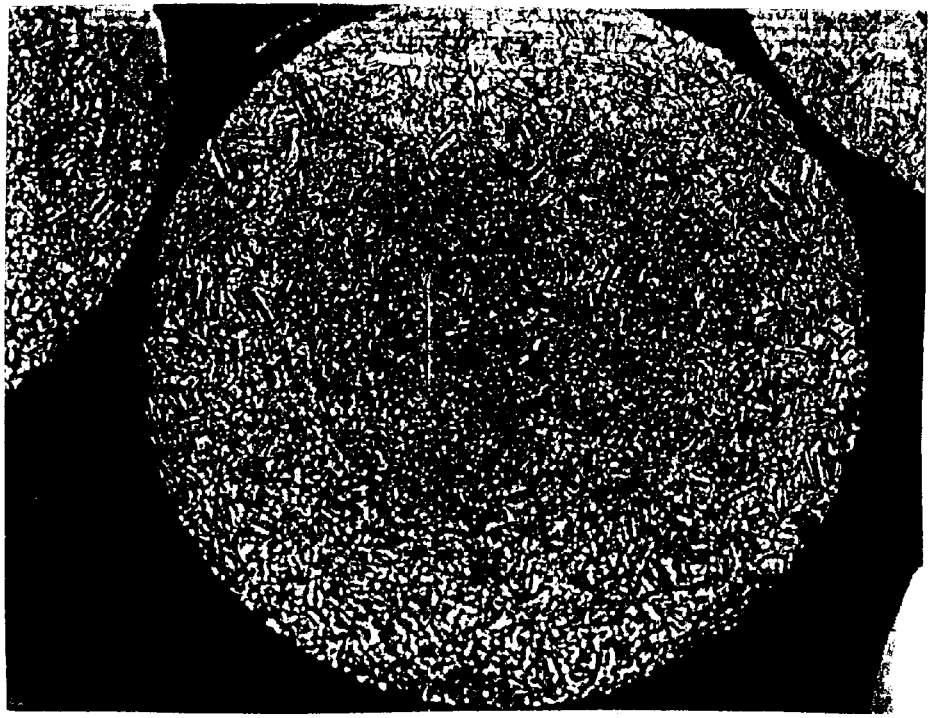
FIG. 19 is a micrograph of the microstructure of one filiment of an Acumed 1.6 mm cobalt chrome cable.
Figure 20:
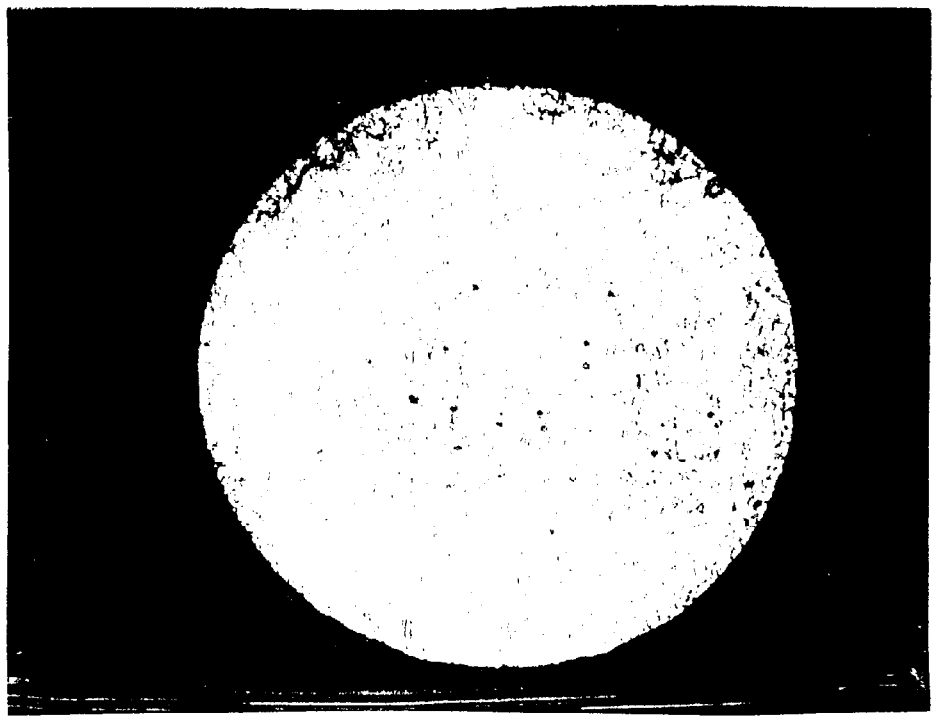
FIG. 20 is a micrograph of the microstructure of one filiment of a Biodynamics 1.6 mm cobalt chrome cable.
Figure 21:
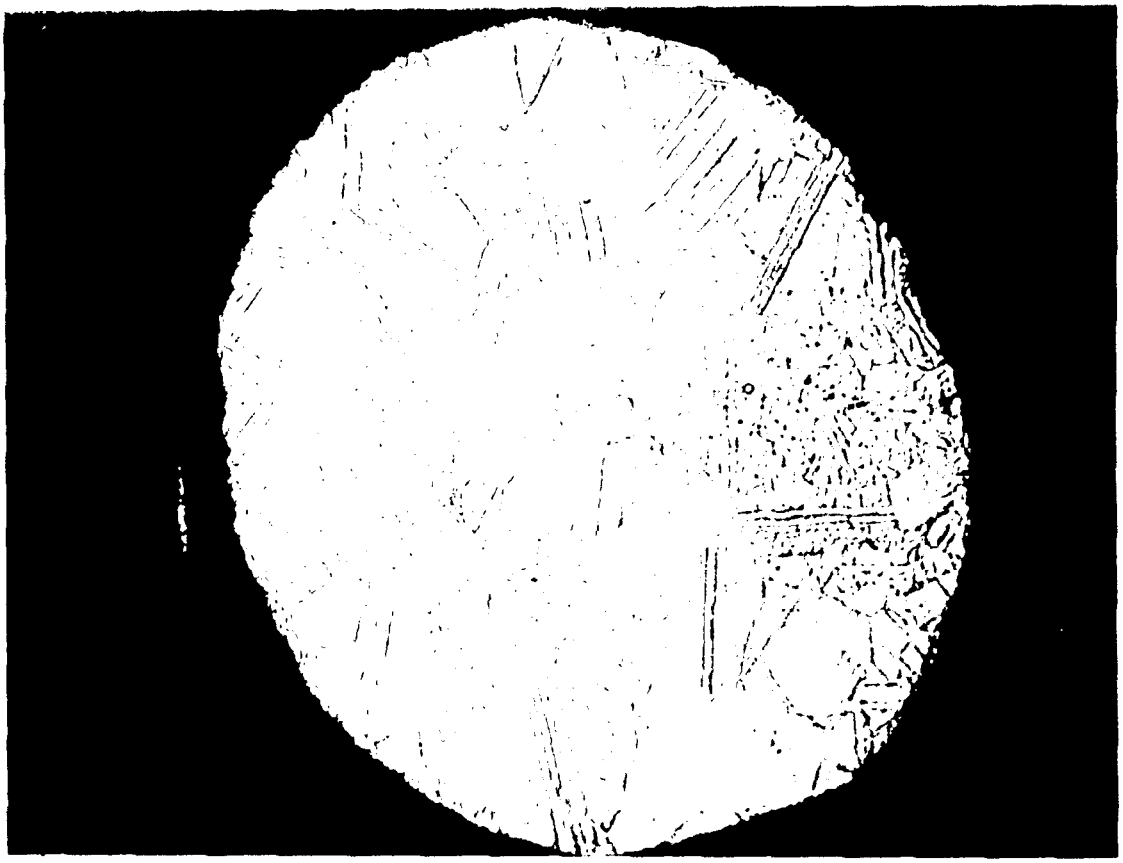
FIG. 21 is a micrograph of the microstructure of one filiment of a Zimmer 1.6 mm cobalt chrome cable.

The Acumed and the Biodynamics cables showed a heavily deformed grain structure with some recrystallized grains as seen in FIGS. 19 and 20 respectively. The Zimmer cable exhibited a fully annealed grain structure with a grain size ASTM #6–7 as shown in FIG. 21.

Fatigue and Tensile Strength Tests

Fatigue and tensile tests were performed on a servo-hydraulic Instron machine (Model 8521). The fatigue test set-up was similar to that shown in FIG. 12. The 2.0 mm and 1.6 mm cables were tested at 880 N and 500 N respectively at a frequency of 10 Hz. Tests were run to 1,000,000 cycles or to failure, whichever occurred first.

The 500 N load was chosen for testing the prototype cables because of the availability of baseline data for the 1.6 mm cable tested at 500 N. In this testing, the stress (load/total cross section area of all wires) applied to the 1.6 mm cable was also used for the 2.0 mm cable. The calculated load for the 2.0 mm cables was 880 N.

The tensile test results are shown in Table 4 which is appended hereto as FIG. 22 and the fatigue test results are shown in Table 5 which is appended hereto as FIG. 23.

Tensile test results showed that the 2.0 mm 280 ksi prototype and 175 ksi prototype cables had a yield strength of 145.7 ksi (1005.3 MPa) and 91.9 ksi (643.0 MPa) respectively as shown at lines two and three of Table 4. The yield strength of original untreated cable (named HOW old in Table 4) was 164.2 ksi (1132.7 MPa). The Acumed and Biodynamics cables had a yield strength of 226 ksi (1559.6 MPa) and 218 ksi ( 1505.0 MPa), higher than the "HOW old" cable. However, their cables had a much lower elongation (3.6–4.2%) than HOW old (7.5%). The 175 ksi cable had an elongation of 68.6%.

Fatigue results showed that the HOW old or the 280 ksi prototype 2.0 mm cables had much higher cycles to failure than the 2.0 mm Acumed or Biodynamics cables when fatigue tested at 880 N. The number of cycles to failure for the 280 ksi cable was almost double that of the HOW old cables (309–340 ksi). The number of cycles to failure for the 175 ksi cable were at least twelve times higher than those of the HOW old cables.

These results also confirmed the hypothesis that the cable fatigue strength is increased when the cable tensile strength is decreased provided that the fatigue test load is much lower than the yield strength.

Similar findings were also found for the 1.6 mm cables. The 280 ksi cable had lower yield strength but high fatigue strength than the original 1.6 mm HOW old cable.

The Zimmer 1.6 mm cable had the lowest yield strength (70.6 ksi/487.3 MPa) of all. It also exhibited the best fatigue resistance under the test force of 500 N; however it has an insufficient tensile strength for orthopedic applications. All four cables did not fail during the fatigue test.

Cold Working Experiments

Three wire filaments were fully annealed at a temperature of 2160 degrees F and then drawn through dies to reduce their diameters and produce permanent strain hardening. Each filament was cold worked by a different amount and the resulting tensile strength of each filament was accordingly different. Table 6, below, illustrates the results of each cold working experiment.

TABLE 6

| Filament | Cold Reduction in Diameter | Tensile strength |
| --- | --- | --- |
| I | 38% | 280 ksi |
| II | 18% | 240 ksi |
| III | approximately 5%–10% | 175 ksi |

There have been described and illustrated herein several embodiments of a orthopaedic cables and wires and methods for making them. While particular embodiments of the invention have been described with reference to cobalt-chrome alloy, it is not intended that the invention be limited thereto, as it is intended that the invention be as broad in scope as the art will allow and that the specification be read likewise. In particular, other alloy systems, such as stainless steel and titanium alloys, are intended to be included within the scope of the invention taught and claimed herein. It will therefore be appreciated by those skilled in the art that yet other modifications could be made to the provided invention without deviating from its spirit and scope as so claimed.

What is claimed is:

1. An orthopaedic cable having an ultimate tensile strength below 1900 MPa but above 1275 MPa and an average life of at least 200,000 cycles when tested at a load of 500 N.

2. An orthopaedic cable according to claim 1 having a 0.2% yield strength below 1005 MPa but above 634 MPa.

3. An orthopaedic cable according to claim 1 wherein said cable is made of cobalt-chromium alloy.

4. An orthopaedic cable according to claim 1 wherein said cable is made of stainless steel alloy.

5. An orthopaedic cable according to claim 1 wherein said cable is made of titanium alloy.

6. An orthopaedic cable according to claim 1 wherein said cable is made by annealing high tensile strength cable.

7. An orthopaedic cable according to claim 1 wherein said cable is made by annealing high tensile strength cable at a temperature between 1550 degrees F and 2050 degrees F.

8. An orthopaedic cable according to claim 1 wherein said cable is made by annealing high tensile strength cable at a temperature of approximately 1950 F.

9. An orthopaedic cable, comprising a plurality of filaments each having a tensile strength below approximately 280 ksi but above approximately 175 ksi.

10. An orthopaedic cable according to claim 9, wherein each of said filaments has a tensile strength below approximately 240 ksi but above approximately 210 ksi.

11. An orthopaedic cable according to claim 9, wherein:

each of said filaments is a chromium-cobalt alloy.

12. An orthopaedic cable according to claim 9, wherein said cable is made by annealing high tensile strength cable.

13. An orthopaedic cable according to claim 9, wherein said cable is made by annealing high tensile strength cable at a temperature between 1550 degrees F and 2050 degrees F.

14. An orthopaedic cable according to claim 9, wherein said cable is made by annealing high tensile strength cable at a temperature of approximately 1950 degrees F.

15. An orthopaedic cable according to claim 9, wherein each filament is made by cold working a fully annealed filament to reduce the diameter of the fully annealed filament by an amount greater than 5% but less than 38%.

16. An orthopaedic cable according to claim 9, wherein each filament is made by cold working a fully annealed filament to reduce the diameter of the fully annealed filament by approximately 18%.

17. A wire filament for use in making an orthopaedic cable, said wire filament having a tensile strength below approximately 280 ksi but above approximately 175 ksi.

18. A wire filament according to claim 17, wherein said wire filament has a tensile strength below approximately 240 ksi but above approximately 210 ksi.

19. A wire filament according to claim 17, wherein said wire filament is a chromium-cobalt alloy.

20. A wire filament according to claim 17, wherein said wire filament is made by annealing high tensile strength wire filament.

21. A wire filament according to claim 17, wherein said wire filament is made by annealing high tensile strength wire filament at a temperature between 1550 degrees F and 2050 degrees F.

22. A wire filament according to claim 17, wherein said wire filament is made by annealing high tensile strength wire filament at a temperature of approximately 1950 degrees F.

23. A wire filament according to claim 17, wherein said wire filament is made by cold working a fully annealed filament to reduce the diameter of the fully annealed filament by an amount greater than 5% but less than 38%.

24. A wire filament according to claim 17, wherein said wire filament is made by cold working a fully annealed filament to reduce the diameter of the fully annealed filament by approximately 18%.

* * * * *

UNITED STATES PATENT AND TRADEMARK OFFICE
CERTIFICATE OF CORRECTION

PATENT NO.    : 6,045,909
DATED         : April 4, 2000
INVENTOR(S)   : Wang et al.

It is certified that error appears in the above-identified patent and that said Letters Patent is hereby corrected as shown below:

Column 2, line 43, cancel the word "be".
Column 2, line 53, "under going" should read "undergoing".
Column 3, line 47, cancel the word "the".
Column 3, line 58, after "is" insert -- a --.
Column 7, line 62, "measurement" should read -- measurements --.
Column 8, line 64, "were" should read -- was --.
Column 9, line 4, "high" should read -- higher --.
Column 9, line 28, cancel the word "a".
Column 9, line 59, "¯" should read -- degrees".

Signed and Sealed this

Twenty-seventh Day of March, 2001

Attest:

NICHOLAS P. GODICI

Attesting Officer

Acting Director of the United States Patent and Trademark Office